United States Patent [19]

Lipman

[11] Patent Number: 6,083,160
[45] Date of Patent: Jul. 4, 2000

[54] APLANATION TONOMETRY APPARATUS

[75] Inventor: Aharon Lipman, Michmoret, Israel

[73] Assignee: Lipman Electronic Engineering Ltd., Tel Aviv, Israel

[21] Appl. No.: 08/860,097

[22] PCT Filed: Dec. 28, 1995

[86] PCT No.: PCT/US95/16909

§ 371 Date: Jul. 2, 1997

§ 102(e) Date: Jul. 2, 1997

[87] PCT Pub. No.: WO96/20635

PCT Pub. Date: Jul. 11, 1996

[30] Foreign Application Priority Data

Jan. 5, 1995 [IL] Israel ........................................ 112264

[51] Int. Cl.[7] ...................................................... A61B 3/16
[52] U.S. Cl. ........................................... 600/398; 600/405
[58] Field of Search ..................................... 600/398–406

[56] References Cited

U.S. PATENT DOCUMENTS 4,987,899  1/1991  Brown .
5,070,875  12/1991  Falck et al. .
5,355,884  10/1994  Bennett .

*Primary Examiner*—John P. Lacyk
*Attorney, Agent, or Firm*—Blank Rome Comisky & McCauley LLP

[57] ABSTRACT

An applanation tonometer including a light-conducting pressure applicator assembly having an end to be placed in contact with the cornea of a subject's eye and an opposite end, a displacer locating said pressure applicator assembly with said end against the subject's cornea thereby flattening a portion thereof, an illuminator for illuminating the subject's cornea, an imaging transducer at the opposite end of the pressure applicator assembly for receiving therethrough an optical image of at least said portion of the subject's cornea and converting said optical image of at least said portion of the subject's cornea into electrical signals representative of the optical image of at least said portion of the subject's cornea and a data processor for receiving the electrical signals representative of the optical image of at least said portion of the subject's cornea, as outputted by said imaging transducer, and utilizing this optical image as well as information indicating an amount of force applied to at least said portion of the subject's cornea for producing an output representing intraocular pressure.

16 Claims, 2 Drawing Sheets

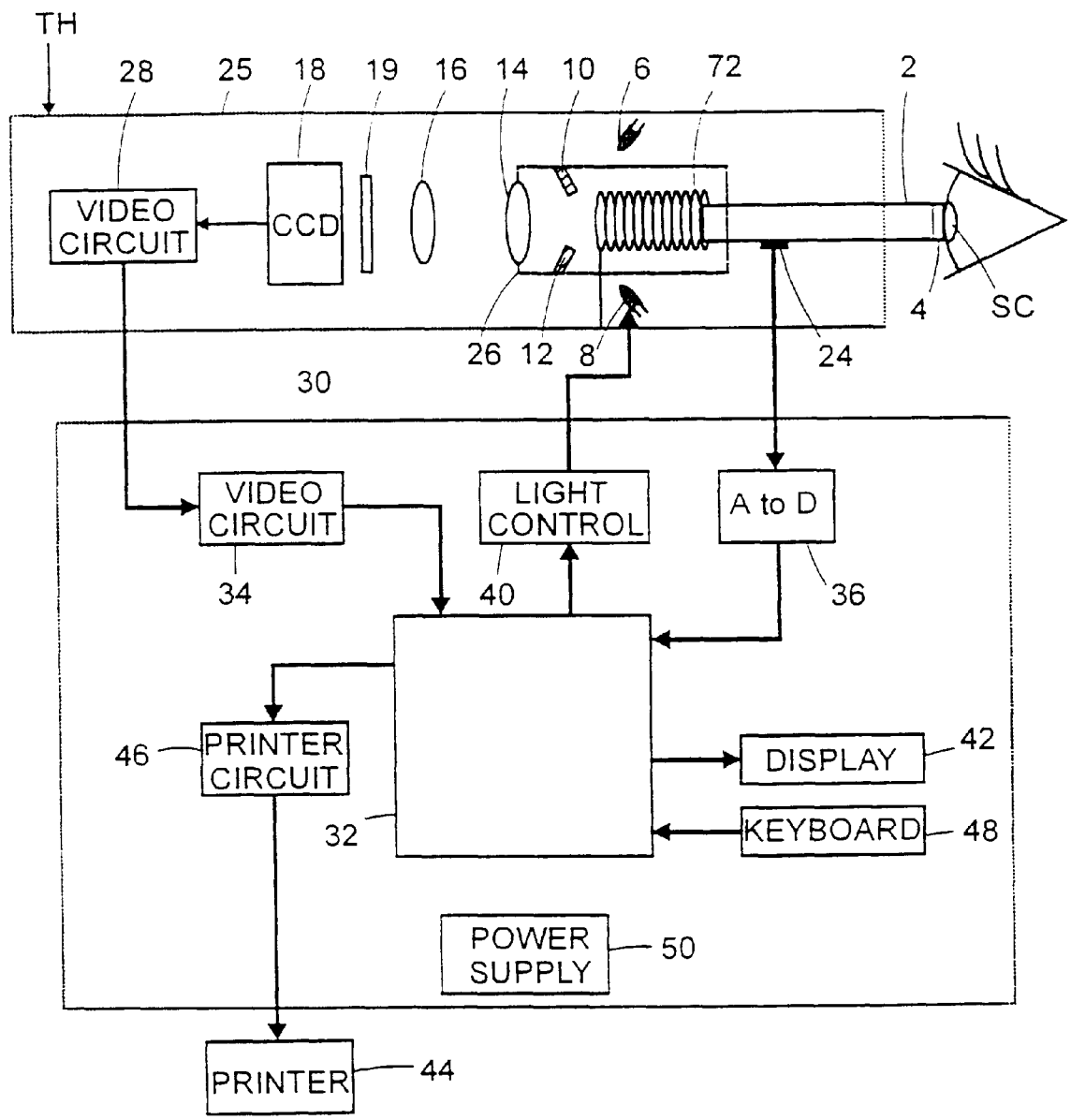
F I G. 2

APLANATION TONOMETRY APPARATUS

FIELD OF THE INVENTION

The present invention relates to tonometry apparatus for measuring the intra-ocular pressure (IOP) of a subject's eye, and particularly to an applanation type tonometer which produces such a measurement by flattening the subject's cornea.

BACKGROUND OF THE INVENTION

The intra-ocular pressure (IOP), i.e., the pressure within the eyeball, of a person is one of the most important parameters indicating the health status of the person's eye. Various eye diseases cause the IOP to be higher or lower than normal, but it is mainly elevated when the patient is suffering from glaucoma. Glaucoma is an extremely common condition afflicting about 2% of the population over 40 years of age and is one of the major causes of blindness in the world. This disease has no symptoms and is usually diagnosed by tonometry measuring the IOP of the subject. Tonometry is therefore a routine procedure in all eye examinations, especially those of adults.

There are various types of tonometers for measuring the IOP. One type, called an "indentation tonometer", or "impression tonometer", measures the IOP by measuring a deformation produced in the subject's cornea when a constant force is applied. However, the more common type is the "applanation tonometer", which flattens the cornea and measures the force applied. The commonest and most reliable tonometer used at the present time is called the Goldmann applanation tonometer, in which a flat plate is pressed against the subject's cornea, and the area of applanation is viewed by means of a split-lamp and microscope until the diameter of applanation is found to be 3.06 mm. Thus, it was found by Goldmann that at an applanation diameter of 3.06 mm (or an applanation area of 7.35 mm$^2$), the force required to distort the cornea from its convex shape to a flat shape counterbalances the surface tension effect of the tear of the subject, such that when using this applanation diameter, the force in grams multiplied by "10" is directly converted to the IOP in mm of Hg.

In the Goldmann tonometer, the applanation area is measured by optically splitting it into two halves by a biprism, one half being displaced 3.06 mm relative to the other. A fluorescent solution is first applied to the eye to form a ring which is seen as two semi-circles. A dial is then manually rotated to apply a flattening force to the subject's cornea. When the two semi-circular rings touch, the position of the dial, calibrated in mm Hg, indicates the force required to produce an applanation diameter of 3.06 mm.

A problem with applanation tonometers in general, and the Goldmann applanation tonometer in particular, is the relatively long contact time between the flat plate and the subject's cornea during the measurement. Not only is a long contact time very unpleasant to the subject, but any movement of the subject's eye during the contact time may require restarting the procedure. This long duration of contact generally requires anesthetizing children, and sometimes adults, in order to make the IOP measurements.

Other drawbacks in the use of the existing Goldmann applanation tonometer for making IOP measurements are the dependence or accuracy on the expertise of the person making the measurements, and the large size and bulkiness of the apparatus used for making such measurements.

SUMMARY OF THE INVENTION

An object of the present invention is to provide an applanation tonometer having advantages in some or all of the above respects.

According to the present invention, there is provided an applanation tonometer comprising: a light-conducting pressure applicator having a flat wall at one end to be placed in contact with the cornea of the subject's eye; force applying means for applying a force to the pressure applicator to displace it against the subject's cornea and thereby to flatten it; an illuminator for illuminating the subject's cornea; an image transducer at the opposite end of the pressure applicator for converting the optical image of the subject's cornea into electrical signals; an optical system at the opposite end of the pressure applicator for imaging the subject's cornea on the image transducer; and a data processor receiving the electrical signals outputted by the image transducer and producing an output corresponding to the force applied by the pressure applicator to the subject's cornea as determined by the flatness of the subject's cornea.

According to further features in the preferred embodiments of the invention described below, the pressure applicator, image transducer, and optical system are all incorporated in a common housing which is movable towards the eye to flatten the cornea. Preferably, the illuminator illuminates the subject's cornea with light of predetermined wavelengths, and the optical system includes a light filter passing only the predetermined wavelength to the image transducer.

Two such tonometers are described below for purposes of examples.

In one described tonometer, the force applying means is controlled by an electrical control signal generated by the date processor in response to the electrical signals received from the image transducer to produce a predetermined flatness of the subject's cornea. Such tonometer is thus based on a closed-loop feedback system.

A second tonometer is described wherein the force applying means applies an increasing force to the pressure applicator, and the data processor receiving the electrical signals from the image transducer produces outputs corresponding to the force applied, thereby enabling determining the force applied when a predetermined flatness in the subject's cornea is sensed. Such a tonometer is thus based on an open-loop non-feedback system.

Applanation tonometers constructed with the foregoing features provides a number of important advantages over the conventional Goldmann applanation tonometer. Thus, the time required for making the measurement may be very substantially reduced. In addition, the accuracy of the measurement is not dependent on the expertise of the person making the measurement. In fact, particularly if a light filter of the illuminator bandwidth is used to increase the signal-to-noise ration, it may even be possible to omit the use of fluorescein, which is generally considered mandatory in the conventional Goldmann tonometry. Further, vertical alignment, which is also mandatory in the conventional Goldmann tonometer, is not required using the tonometer of the present invention. Still further, the tonometer of the present invention provides automatic correction for astigmatism.

Still further, where the force applied by the pressure applicator to flatten the cornea is controlled by an electrical control signal generated by the data processor, as in the first described embodiment, the electrical control signal may be modulated at a frequency of many times (at least five times) the pulse rate of the subject, enabling a calculation to be made (e.g., by suing Fourier Transform analysis) of the dependence of the IOP on cardiac pulsation. The phase difference between the applied force and the measured area provides information on the tear viscosity, enabling a correction to be made because of tear viscosity in the calculation of the IOP. Also, by causing the pressure applicator to apply a constant force to the subject's cornea, and measuring the change of IOP with time, information indicating the facility of outflow of the eye fluid is obtainable (Tonography), which information is also useful in assessing the condition of the subject's eye.

Further features and advantages of the invention will be apparent from the description below.

BRIEF DESCRIPTION OF THE DRAWINGS

The invention is herein described, by way of example only, with reference to the accompanying drawings, wherein:

and FIG. 2 illustrates the applanation tonometer head of FIG. 1 embodied in an open-loop, non-feedback system.

DETAILED DESCRIPTION OF AN EMBODIMENT OF THE INVENTION

Figure 1:
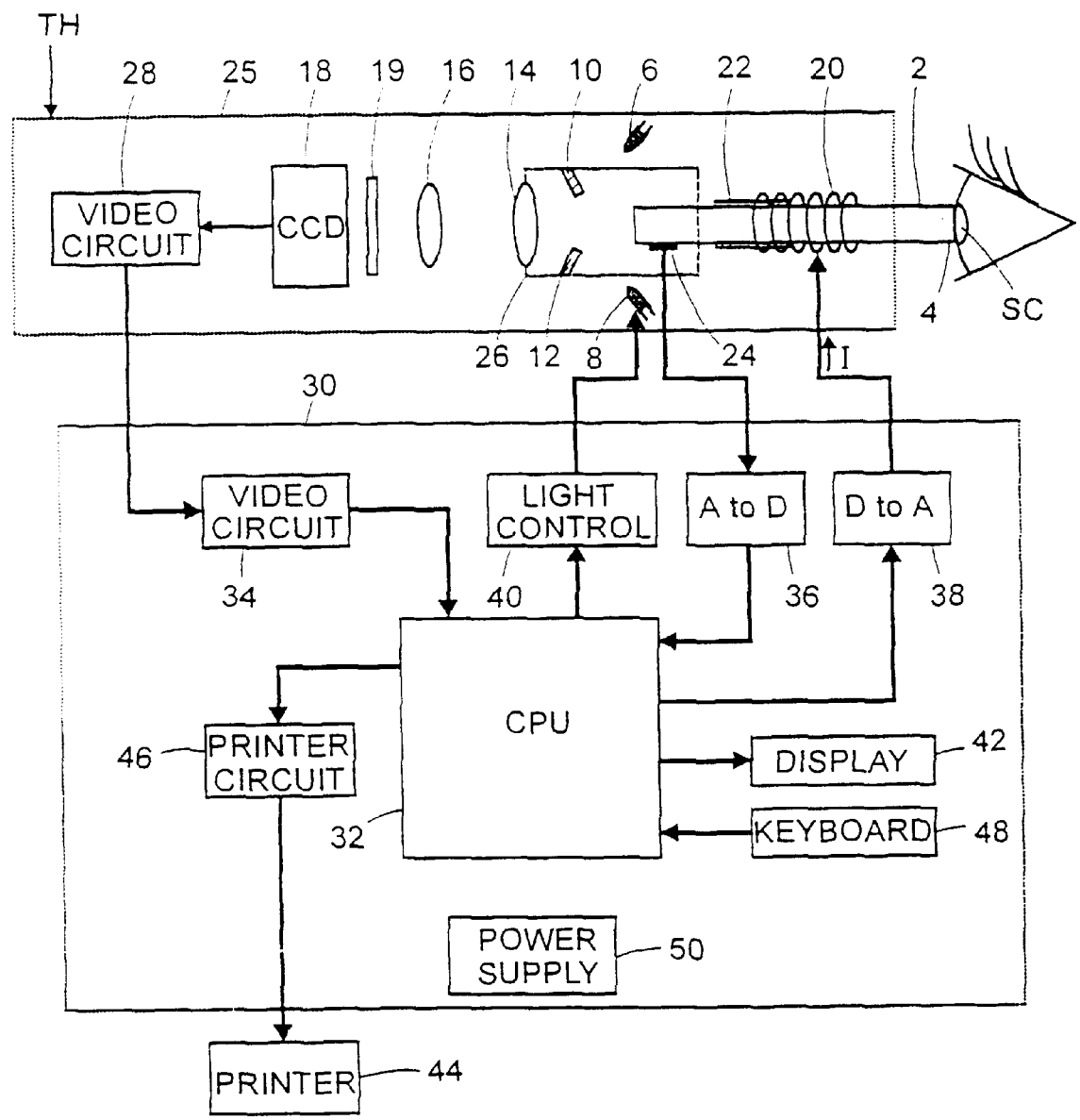
FIG. 1 diagrammatically illustrates the basic elements of one form of applanation tonometer head constructed in accordance with the present invention and a closed-loop feedback system including the applanation tonometer head.

The applanation tonometer head TH illustrated in FIG. 1 comprises a pressure applicator 2 having a flat wall 4 at one end to be pressed into contact with the cornea of the subject's eye, and thereby to flatten the cornea. Pressure applicator 2 may thus be a hollow or solid cylinder of glass or transparent plastic; the flat end wall 4 may be a glass plate, a prism, or biprism made of glass or other transparent material. Flat end wall 4 may be replaceable (for hygienic purposes) or fixed.

The tonometer head TH further includes an illuminator at the end of the pressure applicator 2 opposite to that engaging the subject's cornea, for illuminating the subject's cornea. The illuminator includes a plurality of LEDs (light emitting diodes) 6, 8 at the end of the pressure applicator 2, and a mirror 10, 12 for each LED to reflect the light therefrom through the pressure applicator 2 to the subject's cornea. The light is reflected back from the subject's cornea through the pressure applicator to a collimating lens 14. Lens 14 collimates the light to a focussing lens 16, which focusses the light onto an image transducer 18, preferably a CCD (charge-coupled device) video camera.

Focussing lens 16 thus focusses the image of the cornea, as engaged by the flat glass plate 4, onto the image transducer 18. The image transducer 18 converts the optical image of the subject' cornea into electrical signals.

The LEDs 6, 8 preferably emit short pulses of light (about one microsecond) in a narrow band in the infrared spectrum. A filter 19 is provided between the pressure applicator 2 and the CCD 18 (in this case between lens 16 and the CCD) to pass mainly the predetermined wavelength of the LED light. Such an arrangement minimizes the effects of stray light and thereby increases the signal-to-noise ratio. The wavelength of the light emitted by the LEDs 6, 8 may be selected to maximize the objects being viewed by the CCD. For example, if it is found that the fluorescent rings are best observed at one specific wavelength, while the contour of the area is best observed at another wavelength, the LEDs would be selected to emit the light including the two wavelengths, and the filter 19 would be selected to maximize the transmission of those wavelengths.

The tonometer head illustrated in FIG. 1 further includes means for applying a force to the pressure applicator 2 for displacing it towards the subject's cornea SC in order to flatten the cornea to a predetermined diameter, namely 3.06 mm when the tonometer is used according to the Goldmann technique. For this purpose, the tonometer head includes an electrical coil 20 enclosing the pressure applicator 2 and magnetically coupled to a metal layer 22 on the outer surface of the pressure applicator to apply a displacing force to the pressure applicator according to the current through the coil. The tonometer head TH further includes a position sensor 24 for measuring the position of the pressure applicator 2.

The tonometer head TH illustrated in FIG. 1 is incorporated in a common housing 25, e.g., resembling a pen to be applied against the subject's eye. Collimating lens 14 is mechanically secured to the pressure applicator 2 so that its distance from the end of the pressure applicator remains fixed. This is schematically shown in FIG. 1 by a mechanical connection 26 between lens 14 and the pressure applicator 2. Since the light exiting from collimating lens 14 is substantially parallel, the filter 19, focussing lens 16, and CCD 18 need not, but may be, also mechanically secured to the pressure applicator 2 so as to move with it and with the collimating lens 14.

The electrical signals outputted from the CCD image transducer 18 in the tonometer head TH are processed in a video circuit 28 which may also be within the common housing 25 of the tonometer head.

The electrical output of the video circuit 28 is fed to a data processor, generally designated 30. Data processor 30 includes CPU (central processor unit) 32 which receives the output of the CCD video circuit 28 via another video circuit 34 within the data processor 30. The CPU 32 further receives electrical signals from the position sensor 24 via an analog-to-digital converter 36.

As a result of this inputted information, CPU 32 generates an electrical control signal which is applied via a digital-to-analog converter 38 to the coil 20 to control the current through the coil, and thereby the force applied by the coil to displace the pressure applicator 2. CPU 32 also outputs an electrical signal to a light control unit 40 which controls the current to the LEDs 6, 8, and thereby the pulse-duration and intensity of illumination applied to the subject's cornea SC. CPU 32 further outputs information to a display unit 42, and to a printer 44 via a printer circuit 46.

Information is inputted into the CPU 32 via a keyboard 48. The power to all the electrical units illustrated in FIG. I is supplied by a power supply 50.

The tonometer illustrated in FIG. 1 may be used to measure the IOP of the subject's eye according to the Goldmann technique, as follows:

The tonometer head TH is applied to the subject's eye such that one end of the pressure applicator 2 contacts the subject's cornea. Current is then fed via the CPU 32 to coil 20 to apply a force to the pressure applicator 2, displacing it towards the subject's eye so as to flatten the subject's cornea SC. As this is done, the subject's cornea, illuminated by LEDs 6, 8 and mirrors 10, 12, is imaged via lenses 14, 16 on the CCD 18, which outputs electrical signals via video circuits 28, 34, to the CPU 32.

The CPU 32 continuously computes the applanated (flattened) area of the subject's cornea, and controls the current supplied to the coil 20 so as to produce an applanation area of 7.35 $mm^2$ (corresponding to an applanation diameter of 3.06 mm). CPU 32 also computes the force required to produce the above applanation area, and outputs this value of force via display 42 and also via printer 44. The force value is preferably converted by the CPU 32 to mm of Hg.

The system illustrated in FIG. 1 thus provides feedback control of the force applied by the pressure applicator 2 to the subject's cornea to attain and maintain the predetermined flattened area. The IOP can be continuously observed in the display 42, and/or recorded via the printer 44. Fluctuations in the IOP caused by the subject's respiration and cardiac pulse can also be observed in a real time manner. These fluctuations thus change the electrical signal outputted by the CPU via the D/A converter 38 to the coil 20 in order to maintain the cornea in the predetermined flattened condition and can therefore be observed in the display 42.

In addition, applying a constant force, while measuring the change in the IOP with time, provides a measurement of the "facility of outflow" of the eye fluid, which is also useful in determining the condition of the subject's eye. That is, with the applied external force, the IOP rises; this causes the aqueous humour to be driven out of the eye at a rate faster than normal, and consequently the IOP begins to fall. The rate of change depends on the resistance to aqueous outflow.

Further, by modulating the electrical signal applied to winding 20, a modulated force may be applied by the pressure applicator 2 to the subject's cornea. When such a modulated force is applied, the dependence of the IOP on ocular pulsation may be calculated using, for example, Fourier Transform analysis. Moreover, the phase difference between the applied force and the measured area provides information on the tear viscosity. Since calculation of the IOP depends on tear viscosity, this information enables a correction to be made.

FIG. 2 illustrates a tonometer similar to that described above with respect to FIG. 1, except that the tonometer is included in an open-loop, non-feedback system, rather than in a closed-loop, feedback system as described with respect to FIG. 1. In order to facilitate understanding, the same parts corresponding to those described with respect to FIG. 1 carry the same reference numerals.

A main difference in the tonometer illustrated in FIG. 2, is that a continuously-increasing force is applied to the pressure applicator 2 tending to flatten the subject's cornea SC, and the data processor produces outputs corresponding to the force applied. Thus when the subject's cornea attains the predetermined flatness (an area of 7.35 mm$^2$ according to the Goldmann procedure as described above), as viewed by the CCD 18, the output of the CPU 32 at that time corresponds to the force applied to the pressure applicator at that time.

The pressure applicator 2 may be subjected to a continuously increasing force in any convenient manner, either manually or by machine. For this purpose, the tonometer head TH is provided with a spring 72. One end of the spring is fixed with respect to the housing 25 of the tonometer head TH, whereas the other end bears against the end of the pressure applicator 2. Thus, as the tonometer head is moved, either manually or by machine, towards the subject's eye, the pressure applied by the pressure applicator 2 against the subject's cornea will be increased by the compression of spring 72.

The position sensor 24 generates a signal corresponding to the position of the pressure applicator 2 within the housing 25. This signal is outputted to the CPU 32 via the analog-to-digital converter 36. Since the parameters of spring 72 are known, and the displacement of the pressure applicator 2 is known by the position sensor 24, the CPU can thereby compute the force applied to the pressure applicator when the flattened area, as viewed by the CCD 18, reaches the predetermined value.

The system illustrated in FIG. 2 is otherwise constructed, and operates, in substantially the same manner as described above with respect to FIG. 1.

While the invention has been described with respect to two preferred embodiments, it will be appreciated that these are set forth merely for purposes of example, and that many variations, modifications and other applications of the invention may be made.

I claim:

1. An applanation tonometer comprising:
   a light-conducting pressure applicator assembly having an end adapted to be placed in contact with the cornea of a subject's eye and an opposite end;
   a displacer suitable for locating said pressure applicator assembly with said end against the subject's cornea thereby flattening a portion thereof;
   an illuminator for illuminating the subject's cornea;
   an imaging transducer at the opposite end of the pressure applicator assembly for receiving therethrough an optical image of at least said portion of the subject's cornea and converting said optical image of at least said portion of the subject's cornea into electrical signals representative of the optical image of at least said portion of the subject's cornea; and
   a data processor for receiving the electrical signals representative of the optical image of at least said portion of the subject's cornea, as outputted by said imaging transducer, and utilizing this optical image as well as information indicating an amount of force applied to at least said portion of the subject's cornea for producing an output representing intraocular pressure.

2. The tonometer according to claim 1, wherein pressure applicator assembly comprises a collimating optical system located at said opposite end.

3. The tonometer according to claim 2, wherein said illuminator illuminates at least part of the subject's cornea with light of a predetermined wavelength and also comprising:
   a light filter passing at least mainly said predetermined wavelength to said imaging transducer.

4. The tonometer according to claim 1, wherein said displacer controlled by an electrical control signal from said data processor in response to the electrical signals received from said imaging transducer thereby to produce a predetermined flatness of at least said portion of the subject's cornea.

5. The tonometer according to claim 4, wherein said electrical control signal is modulated at a frequency many times the subject's pulse rate so as to apply a modulated force to the subject's cornea.

6. The tonometer according to claim 4, wherein said displacer comprises an electromagnetic actuator.

7. The tonometer according to claim 2, wherein said displacer applies an increasing force to at least said portion of the subject's cornea.

8. The tonometer according to claim 7, wherein said displacer comprises a spring having one end fixed and an opposite end bearing against said opposite end of the pressure applicator assembly.

9. The tonometer according to claim 8, further including a position sensor for sensing the position of the pressure applicator and for outputting an electrical signal corresponding thereto to said data processor, said data processor utilizing also said latter electrical signal for producing an output corresponding to the force applied.

10. The tonometer according to claim 1, wherein said imaging transducer comprises a charge-coupled device (CCD).

11. The tonometer according to claim 1, wherein said illuminator includes a light-emitting diode (LED) and a mirror for reflecting the light therefrom into said opposite end of the pressure applicator.

12. The tonometer according to claim 11, wherein said LED is energized by a plurality of short pulses.

13. The tonometer according to claim 1, wherein said collimating optical system comprises a collimating lens fixed to said pressure applicator, the tonometer also comprising a focusing lens between said collimating lens and said imaging transducer for focusing the image of at least said portion of the subject's cornea on said imaging transducer.

14. The tonometer according to claim 1, wherein said data processor includes an input keyboard, an output display, and an output printer.

15. The tonometer according to claim 5, wherein said displacer comprises an electromagnetic actuator.

16. The tonometer according to claim 3, wherein said displacer applies an increasing force to at least said portion of the subject's cornea.

* * * * *